US010702407B1

(12) United States Patent
Armer et al.

(10) Patent No.: US 10,702,407 B1
(45) Date of Patent: Jul. 7, 2020

(54) GROWTH STENT FOR CONGENITAL NARROWINGS

(71) Applicant: Renata Medical, Inc., Costa Mesa, CA (US)

(72) Inventors: Dustin Armer, Costa Mesa, CA (US); Eason Abbott, Santa Monica, CA (US)

(73) Assignee: Renata Medical, Inc., Costa Mesa, CA (US)

( * ) Notice: Subject to any disclaimer, the term of this patent is extended or adjusted under 35 U.S.C. 154(b) by 0 days.

(21) Appl. No.: 16/441,201

(22) Filed: Jun. 14, 2019

Related U.S. Application Data

(60) Provisional application No. 62/811,875, filed on Feb. 28, 2019.

(51) Int. Cl.
| | |
|---|---|
| *A61F 2/90* | (2013.01) |
| *A61F 2/915* | (2013.01) |
| *A61F 2/95* | (2013.01) |
| *A61F 2/958* | (2013.01) |
| *A61F 2/24* | (2006.01) |
| *A61F 2/07* | (2013.01) |
| *A61F 2/82* | (2013.01) |

(52) U.S. Cl.
CPC ............... *A61F 2/915* (2013.01); *A61F 2/95* (2013.01); *A61F 2/07* (2013.01); *A61F 2/243* (2013.01); *A61F 2/2418* (2013.01); *A61F 2/82* (2013.01); *A61F 2/90* (2013.01); *A61F 2/958* (2013.01); *A61F 2002/91575* (2013.01); *A61F 2210/0014* (2013.01); *A61F 2210/0057* (2013.01); *A61F 2230/0069* (2013.01); *A61F 2250/001* (2013.01); *A61F 2250/0039* (2013.01); *A61F 2250/0082* (2013.01)

(58) Field of Classification Search
CPC ......... A61F 2/07–2002/077; A61F 2/24–2475; A61F 2/82–945; A61F 2250/0082; A61F 2210/0019–0023; A61F 2250/001
See application file for complete search history.

(56) References Cited

U.S. PATENT DOCUMENTS

| | | | |
|---|---|---|---|
| 7,156,869 B1 * | 1/2007 | Pacetti | ...................... A61F 2/91 606/192 |
| 7,318,837 B2 | 1/2008 | Krivoruchko et al. | |
| 8,512,395 B2 | 8/2013 | Meyer et al. | |
| | | (Continued) | |

FOREIGN PATENT DOCUMENTS

WO     WO 2019/033026 A1     2/2019

OTHER PUBLICATIONS

International Search Report and Written Opinion, Application No. PCT/US2019/037448, dated Nov. 15, 2019.

*Primary Examiner* — Rebecca S Preston
(74) *Attorney, Agent, or Firm* — Orrick, Herrington & Sutcliffe, LLP

(57) ABSTRACT

A growth stent and methods for making and using the same. The growth stent may be delivered to treat early stage congenital lesions, while expanding to adult vessel diameters. In selected embodiments, the growth stent can comprise a frame and may have a covering on some portion to prevent blood flow through a wall of the frame. The growth stent advantageously can maintain radial strength across an entire range of diameters necessary to treat a narrowed lesion from birth and childhood through adulthood as the vessels grow over the lifetime of a patient.

27 Claims, 15 Drawing Sheets

(56) References Cited

U.S. PATENT DOCUMENTS

| | | |
|---|---|---|
| 8,647,378 B2 | 2/2014 | Mews et al. |
| 8,870,943 B2 | 10/2014 | Nielsen |
| 9,364,322 B2 | 6/2016 | Conklin et al. |
| 9,375,310 B2 | 6/2016 | Chung et al. |
| 9,381,103 B2 | 7/2016 | Abunassar |
| 9,655,752 B2 | 5/2017 | Shanov et al. |
| 9,737,422 B2 | 8/2017 | Armstrong et al. |
| 10,022,252 B2 | 7/2018 | Shields et al. |
| 10,080,653 B2 | 9/2018 | Conklin et al. |
| 10,220,192 B2 | 3/2019 | Drasler et al. |
| 10,543,085 B2 | 1/2020 | Chung et al. |
| 2002/0128706 A1 | 9/2002 | Osypka |
| 2003/0040792 A1* | 2/2003 | Gabbay ............... A61F 2/2418 623/2.11 |
| 2003/0065386 A1 | 4/2003 | Weadock |
| 2006/0100695 A1 | 5/2006 | Peacock, III et al. |
| 2008/0004696 A1 | 1/2008 | Vesely |
| 2008/0114452 A1* | 5/2008 | Gabbay ............... A61F 2/2412 623/2.42 |
| 2008/0154351 A1 | 6/2008 | Leewood et al. |
| 2008/0221666 A1 | 9/2008 | Licata et al. |
| 2008/0262594 A1 | 10/2008 | Morris |
| 2009/0118810 A1 | 5/2009 | Klein et al. |
| 2009/0248133 A1 | 10/2009 | Bloom et al. |
| 2010/0040663 A1 | 2/2010 | McAllister et al. |
| 2010/0049306 A1 | 2/2010 | House et al. |
| 2010/0122698 A1 | 5/2010 | Shaffer et al. |
| 2010/0256737 A1* | 10/2010 | Pollock ............... A61F 2/91 623/1.15 |
| 2012/0158125 A1* | 6/2012 | Obradovic ............... A61F 2/91 623/1.16 |
| 2013/0073023 A1 | 3/2013 | Mongrain et al. |
| 2013/0211489 A1 | 8/2013 | Makower et al. |
| 2013/0274872 A1 | 10/2013 | Vesely |
| 2015/0202065 A1 | 7/2015 | Shalev et al. |
| 2016/0008130 A1 | 1/2016 | Hasin |
| 2017/0000603 A1 | 1/2017 | Conklin et al. |
| 2017/0014228 A1* | 1/2017 | Emani ............... A61F 2/2418 |
| 2017/0216062 A1 | 8/2017 | Armstrong et al. |
| 2018/0185147 A1 | 7/2018 | Delaloye |
| 2018/0200041 A1 | 7/2018 | Rasmussen et al. |
| 2018/0325651 A1 | 11/2018 | Sumanasinghe et al. |
| 2019/0125517 A1 | 5/2019 | Cully et al. |

* cited by examiner

2mm

8mm

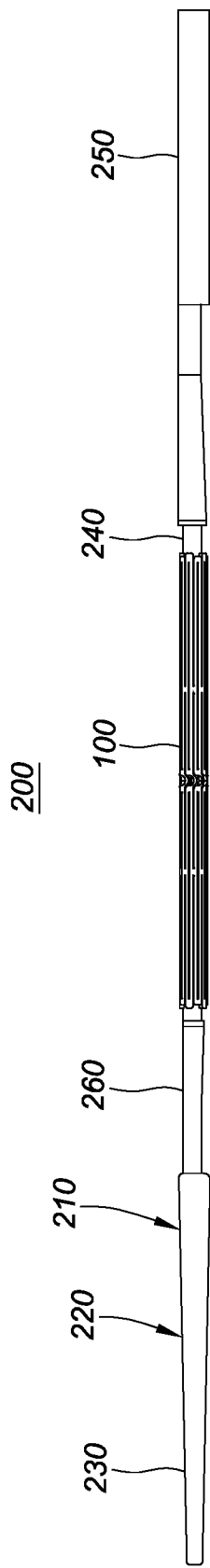
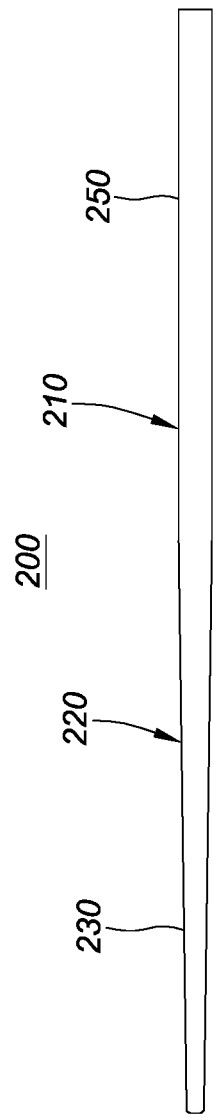
FIG. 7A
FIG. 7B

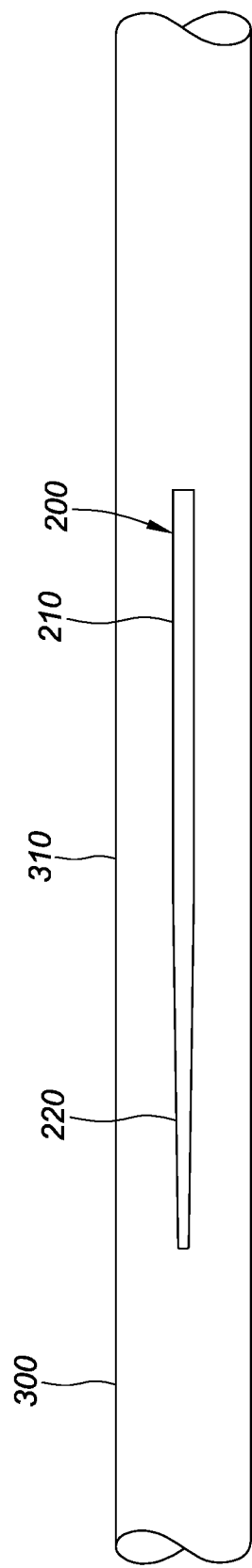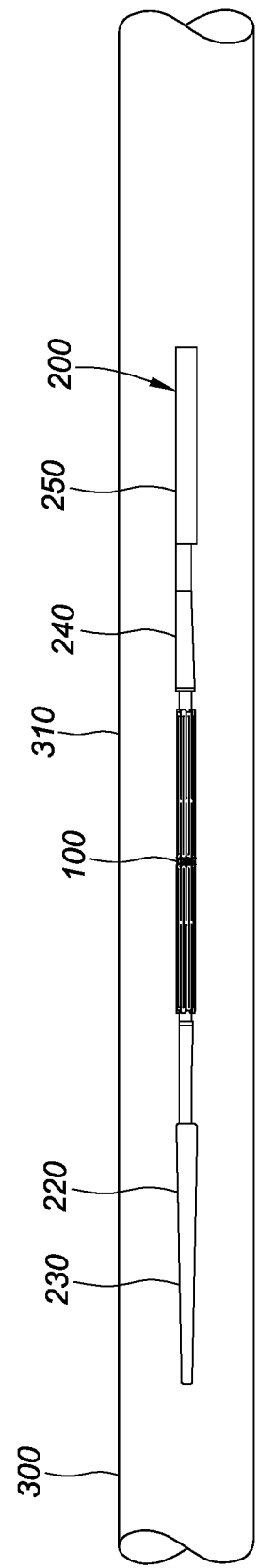

GROWTH STENT FOR CONGENITAL NARROWINGS

CROSS-REFERENCE TO RELATED APPLICATIONS

This application claims the benefit of, and priority to, U.S. Provisional Application Ser. No. 62/811,875, filed Feb. 28, 2019, the disclosure of which is hereby incorporated herein by reference in its entirety and for all purposes.

FIELD

The disclosed embodiments relate to medical stents and more particularly, but not exclusively, to a growth stent for implantation in young patients and subsequent expansion to adult vessel sizes as the patients grow, maintaining proper strength for vessel opening throughout an entire range of expansion.

BACKGROUND

Stents have been used for many years to treat vessel disorders by allowing flow and/or preventing vessel narrowing. Narrowing vessels disrupt blood flow and can create pressure imbalances in the vasculature. Such conditions can eventually lead to serious cardiovascular compromise and/or death. For many years the definitive treatment for such disorders was the surgical repair or replacement of the vessel segment through open heart surgery, but such surgeries are dangerous and prone to complication. Open heart surgery in neonatal and young patients may lead to negative developmental effects.

Stents have also been utilized for holding vessels open, but the growth of the patient prevents stents from being implanted at early development states as they would not be able to grow to the adult sizes. Typically, stents have specific, limited ranges of operation.

In view of the foregoing, a need exists for an improved stent for implantation in young patients and subsequent expansion as the patients grow that overcomes the aforementioned obstacles and deficiencies of currently-available stents.

BRIEF DESCRIPTION OF THE DRAWINGS

FIG. 7A is exemplary detail diagram illustrating an embodiment of a catheter delivery system for implanting the growth stent of FIGS. 1A-B.

FIG. 7B is exemplary detail diagram illustrating an alternative embodiment of the catheter delivery system of FIG. 7A, wherein the catheter delivery system is shown in a closed configuration.

FIG. 8A is exemplary detail diagram illustrating an embodiment of the catheter delivery system of FIGS. 7A-B, wherein a delivery catheter of the catheter delivery system is disposed adjacent to an implantation site.

FIG. 8B is exemplary detail diagram illustrating an embodiment of the catheter delivery system of FIG. 8A, wherein the catheter delivery system is shown in an open configuration.

Figure 1A:
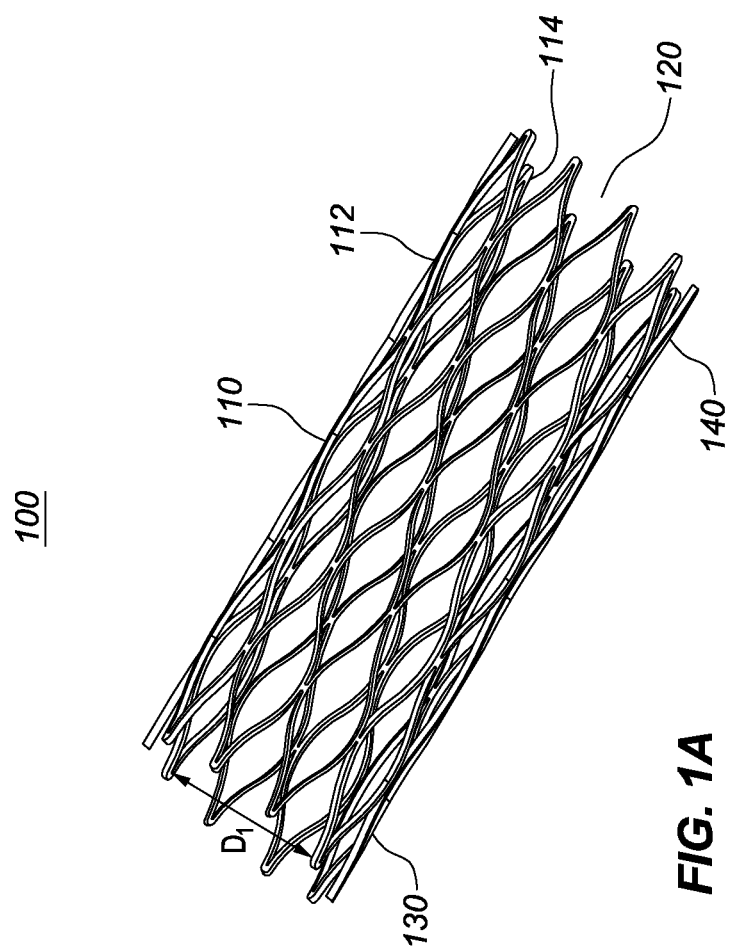
FIG. 1A is an exemplary detail diagram illustrating an exemplary embodiment of a growth stent in a first expanded state.

It should be noted that the figures are not drawn to scale and that elements of similar structures or functions may be generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

Since currently-available stents have specific, limited ranges of operation and, when implanted at early development states are unable to grow to adult sizes, an expandable growth stent that can maintain proper strength throughout a predetermined expansion range can prove desirable and provide a basis for a wide range of system applications, such as implantation in neonates and other young patients and subsequent expansion as the patients grow. This result can be achieved, according to selected embodiments disclosed herein, by a growth stent 100 as illustrated in FIGS. 1A-B.

Figure 1B:
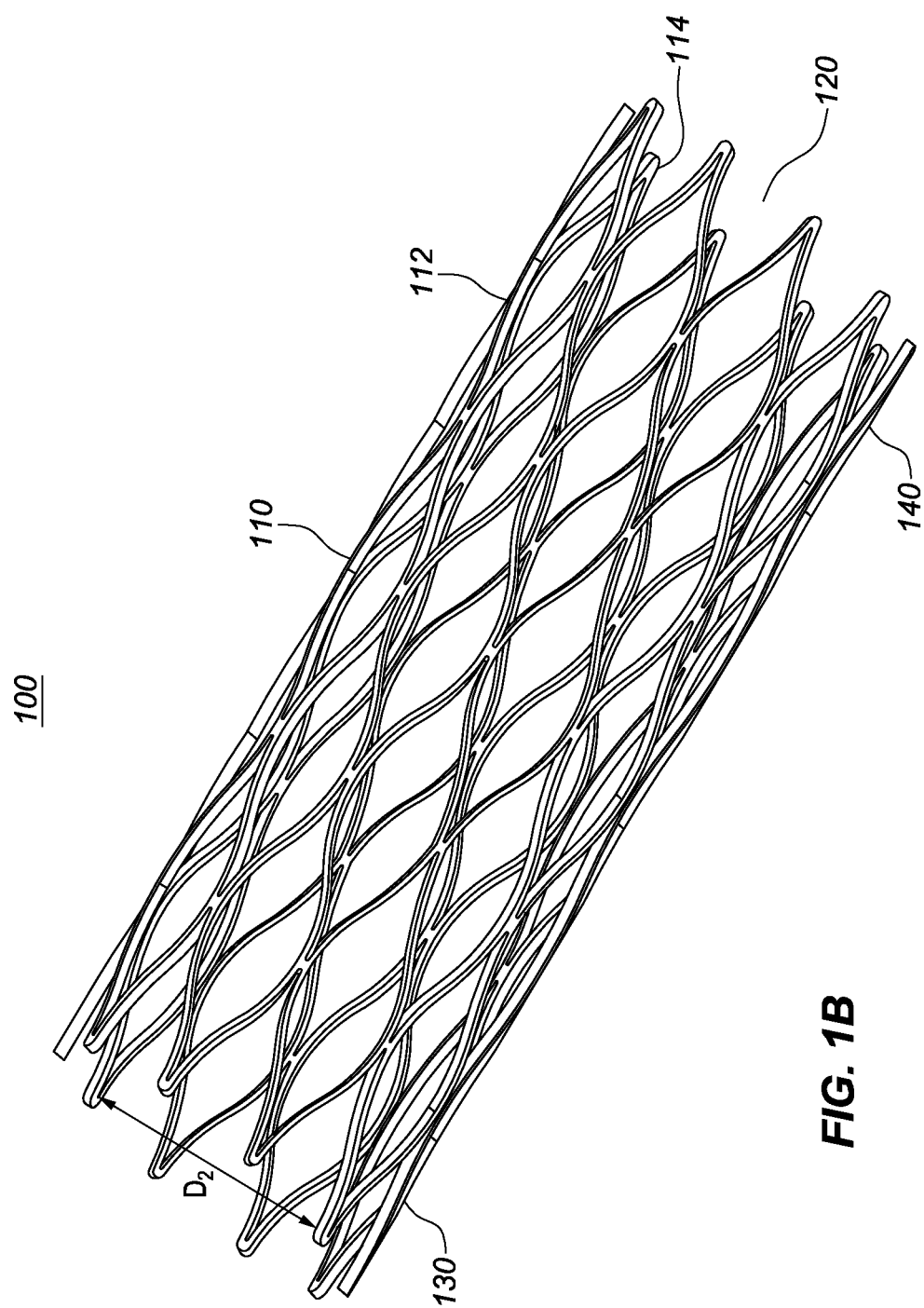
FIG. 1B is an exemplary detail diagram illustrating an alternative embodiment of the growth stent of FIG. 1A, wherein the growth stent is shown in a second expanded state.
Figure 2A:
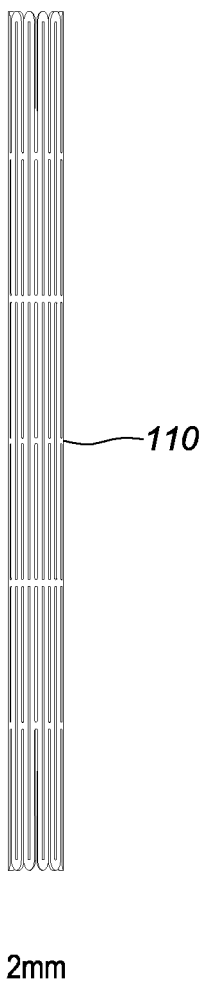
FIG. 2A is an exemplary detail diagram illustrating an embodiment of the growth stent of FIGS. 1A-B, wherein the growth stent is shown in an initial state for implantation.

Turning to FIG. 1A, the growth stent 100 is shown as including an elongated stent frame (or body) 110 for forming an internal channel 120. The growth stent 100 can be implanted within a vessel (or lumen) 300 (shown in FIGS. 8A-D) of a patient to hold open or otherwise reinforce the lumen 300. The stent body 110 can be provided in an initial (or unexpanded or crimped) state as shown in FIG. 2A. In the initial state, the stent body 110 can have any predetermined initial size, shape, diameter, cross-section and/or other dimension for facilitating insertion of the growth stent 100 into the lumen 300. The initial size, shape, diameter, cross-section and/or other dimension D of the stent body 110 can be application dependent.

Upon being positioned at a selected implantation site 310 (or other area of interest) (shown in FIGS. 8A-D) within the lumen 300, the stent body 110 can be expanded from the initial state to a first expanded state as shown in FIG. 1A. In the first expanded state, the stent body 110 can have a first predetermined expanded size, shape, diameter, cross-section and/or other dimension D. The stent body 110, when expanded in the first expanded state, can define the internal channel 120. The internal channel 120 can have a first predetermined diameter, cross-section and/or other dimension $D_1$ for facilitating an unobstructed (or normal) flow of a bodily fluid, such as blood, bile or other luminal liquids, through the lumen 300 via the growth stent 100.

In selected embodiments, the expanded stent body 110 can comprise a body wall 112 that defines the internal channel 120. The body wall 112, for example, can include an inner surface 114 for defining the internal channel 120. The internal channel 120 preferably extends from a proximal end region 130 of the stent body 110 to a distal end region 140 of the stent body 110 as illustrated in FIG. 1A. The growth stent 100 thereby can enable the bodily fluid to flow, preferably unobstructed, from the proximal end region 130 to the distal end region 140 via the internal channel 120. Stated somewhat differently, the growth stent 100 can be provided in generally tubular shape.

Advantageously, the stent body 110 can be further expanded from the first expanded state to a second expanded state as shown in FIG. 1B. The stent body 110 can be expanded to the second expanded state based upon one or more preselected criteria. Exemplary preselected criteria can include, but are not limited to, a preselected duration after implantation of the growth stent 100, a condition of the lumen 300 and/or growth (or other change in size or other condition) of the patient. In the second expanded state, the stent body 110 can have a second predetermined expanded size, shape, diameter, cross-section and/or other dimension, which is greater than the first predetermined expanded size, shape, diameter, cross-section and/or other dimension of the stent body 110.

The stent body 110, when expanded in the second expanded state, can define the internal channel 120 with a second predetermined diameter, cross-section and/or other dimension $D_2$ for maintaining the unobstructed flow of bodily fluid through the lumen 300 via the further-expanded growth stent 100. Stated somewhat differently, the stent body 110 can be provided with a tubular shape and/or can have relatively wide securing end portions (not shown) at the proximal and distal end regions 130, 140 when expanded in the second expanded state. Although shown and described as having two expanded states with reference to FIGS. 1A-B for purposes of illustration only, the growth stent 100 can support any predetermined number of expanded states. The stent body 110, when expanded in a selected expanded state, can define the internal channel 120 with a respective predetermined diameter, cross-section and/or other dimension for maintaining the unobstructed flow of bodily fluid through the lumen 300 via the growth stent 100. The predetermined number of expanded states and the associated predetermined diameters, cross-sections and/or other dimensions, for example, can be application-dependent.

The growth stent 100 advantageously can be expanded to cover the wide range of anatomical diameters necessary to treat narrowed lesions across an entire lifetime of the patient. Stated somewhat differently, the predetermined number of expanded states supported by the growth stent 100 can configure the growth stent 100 to provide a wide range of anatomical diameters. The growth stent 100, for example, can be crimped on the delivery catheter 210 at small enough sizes for a neonatal patient, such as considerably less than an 8 French crimped growth stent 100, with an ability to be expanded later to teen and/or adult sizes of greater than 18 mm in diameter.

FIGS. 2A-D illustrate selected embodiments of a growth stent frame at various cycles throughout a patient's life, as the diameter of a vessel (or lumen) 300 (shown in FIGS. 8A-D) of the patient grows. In this specific example, the growth stent frame 110 can maintain strength at the various diameters. Turning to FIG. 2A, the growth stent 100 is shown in the initial state for implantation. The stent body 110, in the initial state, can have a predetermined initial size, shape, diameter, cross-section or other dimension of, for example, 2 mm for facilitating insertion of the growth stent 100 into the lumen 300.

Figure 2B:
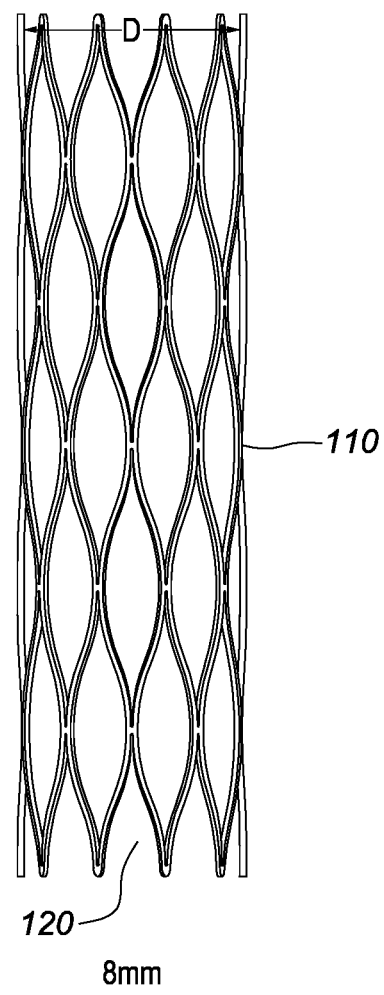
FIG. 2B is an exemplary detail diagram illustrating another alternative embodiment of the growth stent of FIGS. 1A-B, wherein the growth stent is shown in an expanded state for defining an internal channel with a first predetermined cross-section.
Figure 2D:
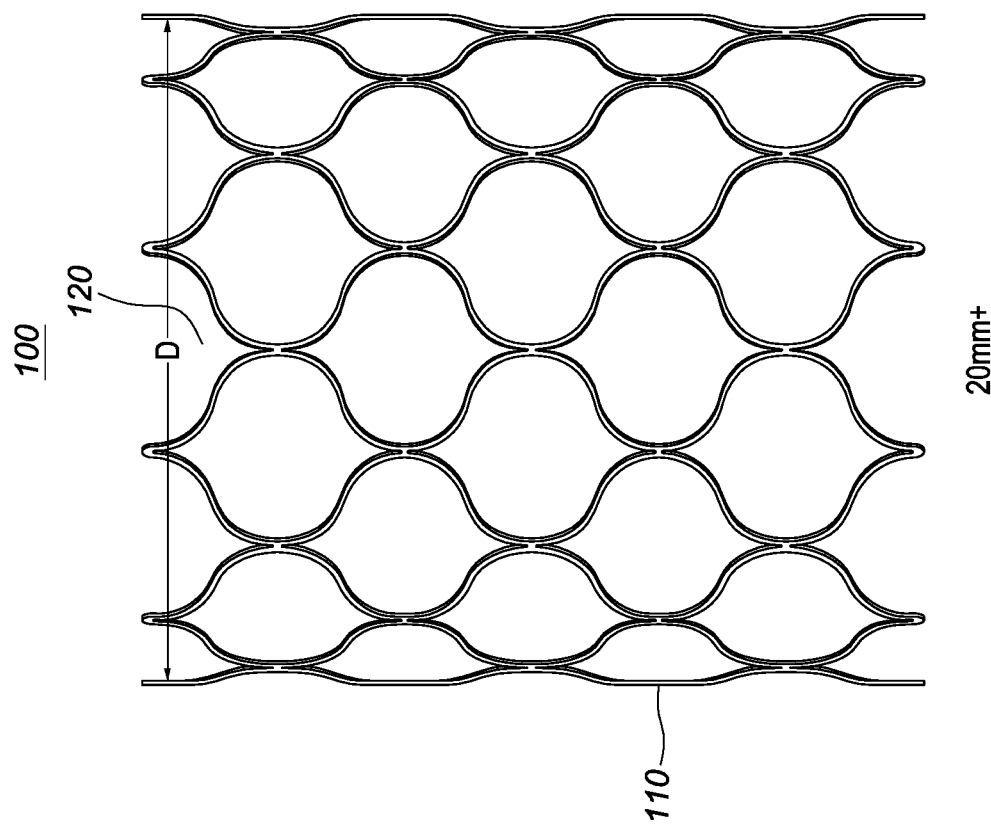
FIG. 2D is an exemplary detail diagram illustrating still another alternative embodiment of the growth stent of FIGS. 1A-B, wherein the growth stent is shown in an expanded state for defining the internal channel with a third predetermined cross-section.
Figure 2C:
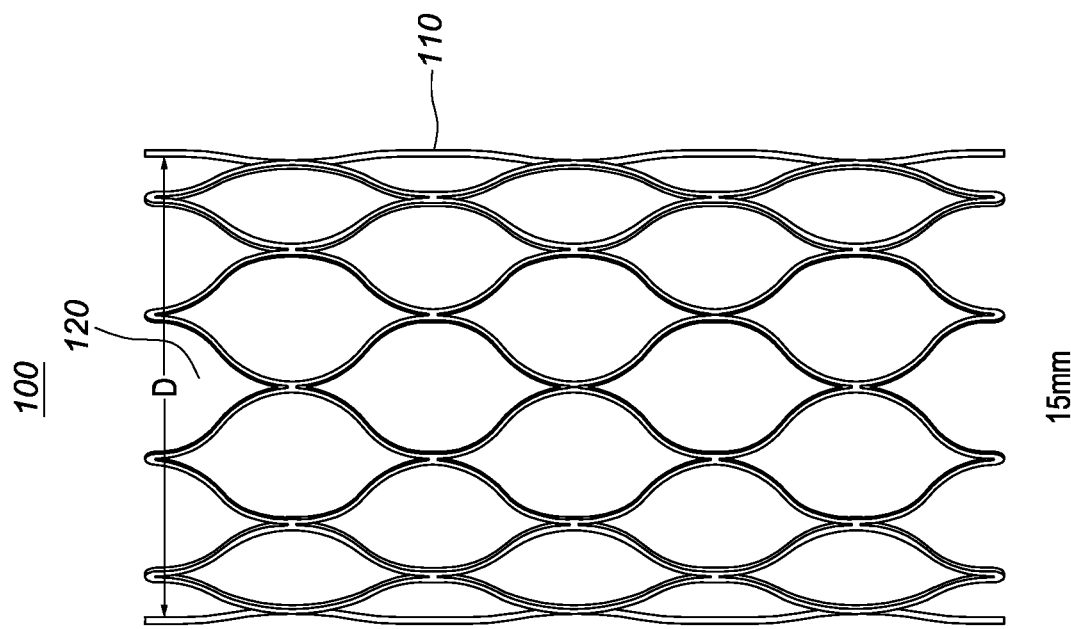
FIG. 2C is an exemplary detail diagram illustrating yet another alternative embodiment of the growth stent of FIGS. 1A-B, wherein the growth stent is shown in an expanded state for defining the internal channel with a second predetermined cross-section.

When the growth stent 100 is in an expanded state, the stent body 110 can define the internal channel 120 with any suitable predetermined diameter, cross-section or other dimension D. The stent body 110, for example, can define the internal channel 120 with a first predetermined diameter, cross-section or other dimension D of 8 mm as shown in FIG. 2B, a second predetermined diameter, cross-section or other dimension D of 15 mm as shown in FIG. 2C and/or a third predetermined diameter, cross-section or other dimension D of 20 mm or more as shown in FIG. 2D, without limitation. The growth stent 100 thereby can be provided to hold open a narrow vessel 300 (shown in FIGS. 8A-D) and allow for normal flow of blood or other bodily fluids.

As an example, the growth stent 100 can be implanted in a vessel (or lumen) 300 (shown in FIGS. 8A-D) of an infantile patient through expansion to a diameter of less than 10 mm and have proper strength to be expanded over the course of a patient's lifetime to significantly greater than 18 mm. The exemplary growth stent 100 can be tracked through the vessel 300 of the infantile patient via a delivery catheter 210 of a catheter delivery system 200 (collectively shown in FIGS. 7A-B) that is considerably less than 8 French in diameter and, in some embodiments, less than 5 French in diameter and beyond.

Figure 3A:
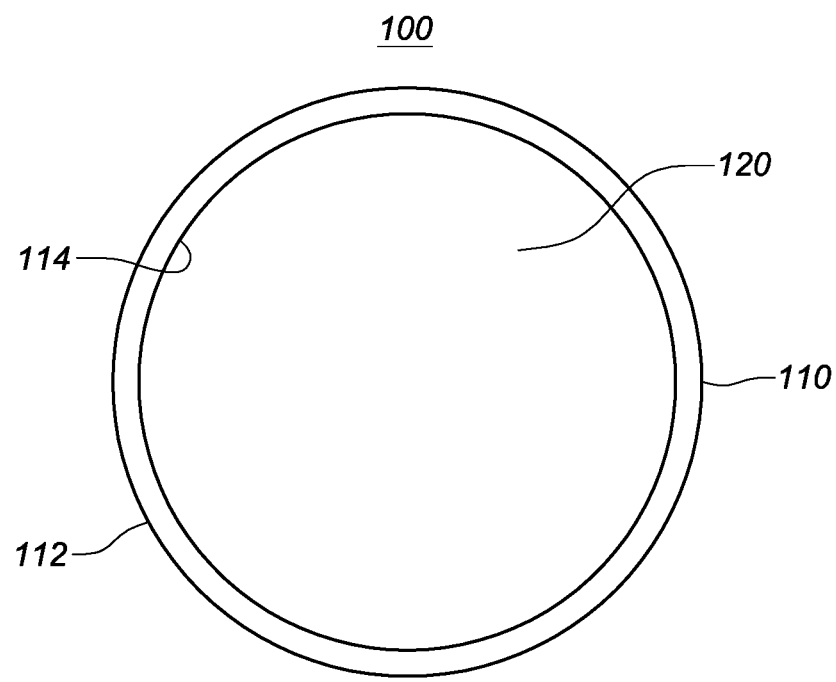
FIG. 3A is an exemplary detail diagram illustrating another alternative embodiment of the growth stent of FIGS. 1A-B, wherein the internal channel comprises an open channel.
Figure 3B:
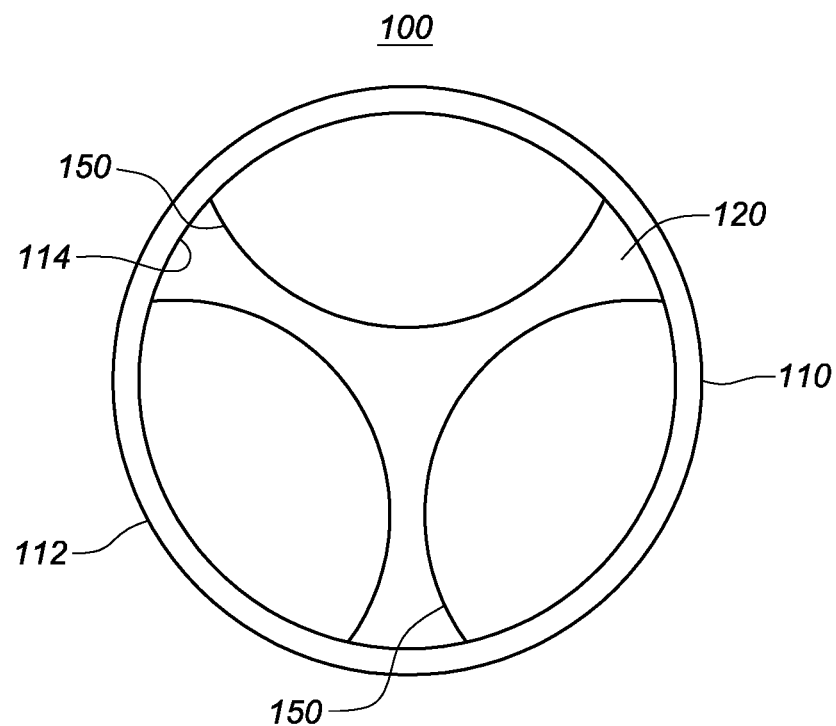
FIG. 3B is an exemplary detail diagram illustrating an alternative embodiment of the growth stent of FIG. 3A, wherein the growth stent includes one or more leaflets extending into the internal channel.

When provided with the tubular shape, the channel 120 formed by the stent body 110 can comprise an open channel in the manner illustrated in FIG. 3A. The growth stent 100 optionally can support a valvular function. In selected embodiments, for example, the growth stent 100 can include one or more leaflets 150 as shown in FIG. 3B. The leaflets 150 can be attached to the inner surface 114 of the body wall 112 and extend into the channel 120 formed by the stent body 110. The leaflets 150 thereby can provide the valvular function via the growth stent 100.

Figure 4A:
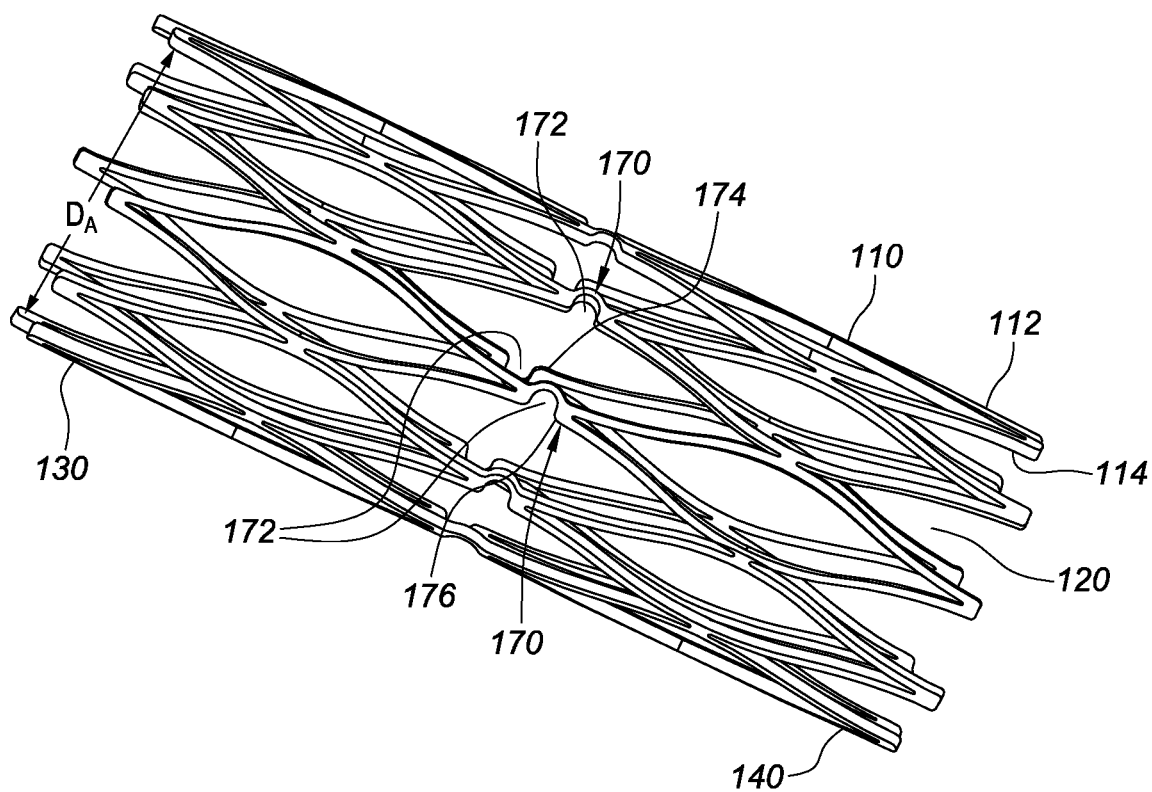
FIG. 4A is an exemplary detail diagram illustrating further alternative embodiment of the growth stent of FIGS. 1A-B, wherein the growth stent includes a plurality of arcuate members.
Figure 4B:
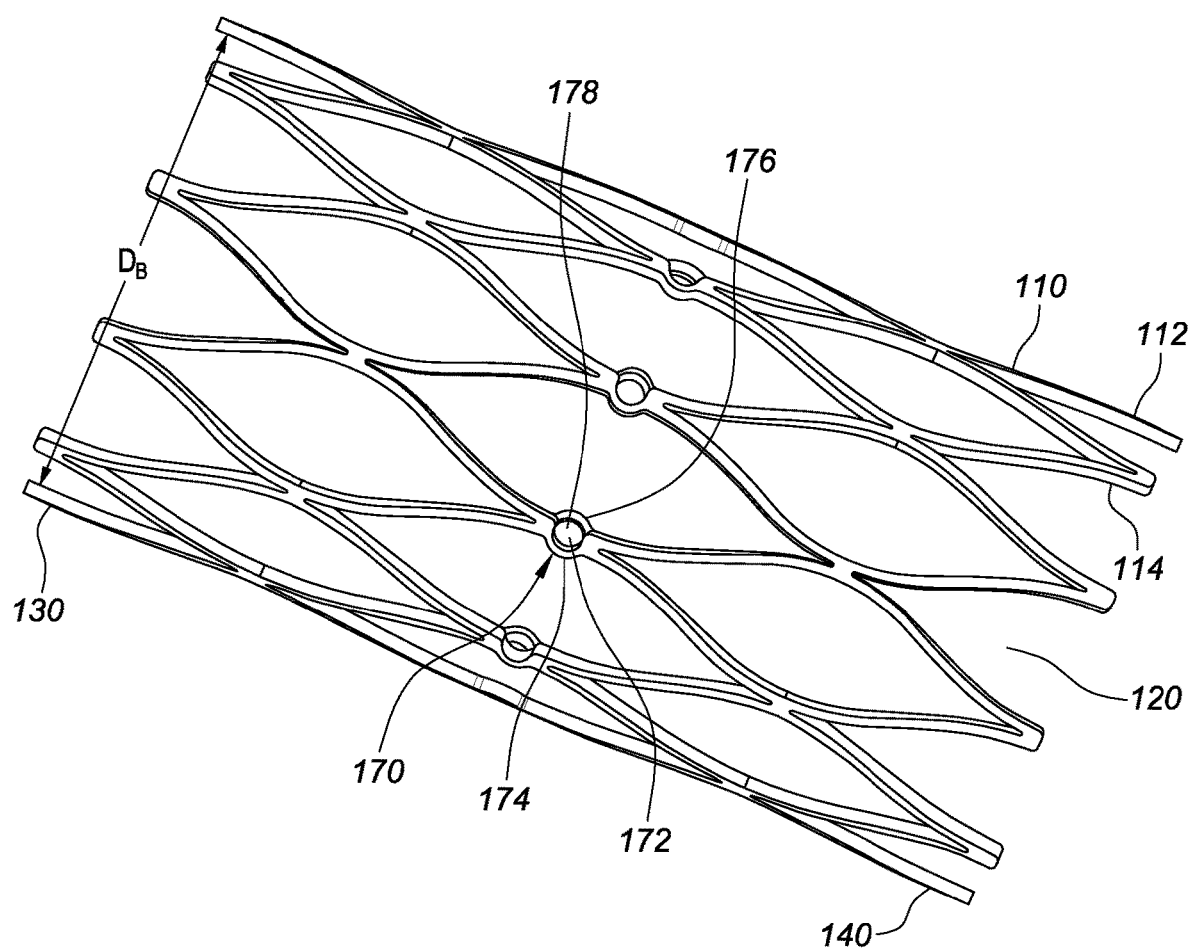
FIG. 4B is an exemplary detail diagram illustrating further alternative embodiment of the growth stent of FIG. 4A, wherein pairs of the arcuate members cooperate.

An alternative embodiment of the growth stent 100 is shown in FIGS. 4A-B. Turning to FIG. 4A, the growth stent 100 is shown as including an elongated stent frame (or body) 110 for forming an internal channel 120. In the manner discussed in additional detail with reference to FIGS. 1A-B, the growth stent 100 can be implanted within a vessel (or lumen) 300 (shown in FIGS. 8A-D) of a patient to hold open or otherwise reinforce the lumen 300. The stent body 110 can be provided in an initial (or unexpanded or crimped) state as shown in FIG. 5A. In the initial state, the stent body 110 can have any predetermined initial size, shape, diameter, cross-section and/or other dimension for facilitating insertion of the growth stent 100 into the lumen 300. The initial size, shape, diameter, cross-section and/or other dimension D of the stent body 110 can be application dependent.

Figure 5B:
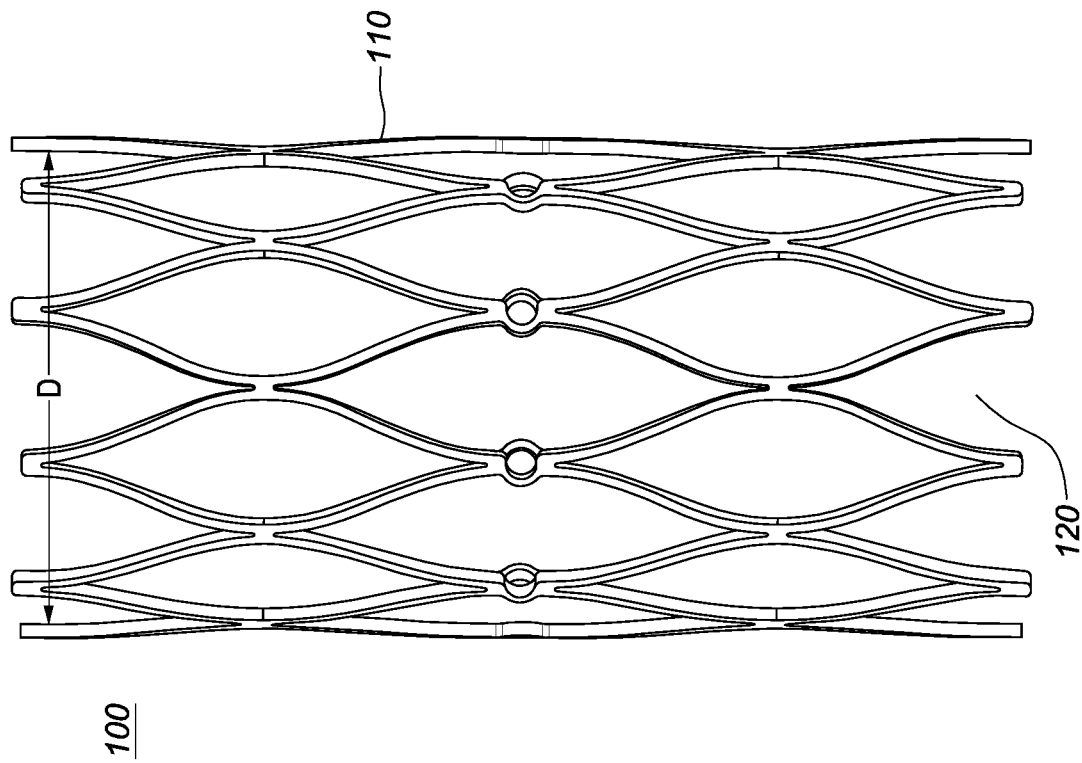
FIG. 5B is an exemplary detail diagram illustrating another alternative embodiment of the growth stent of FIGS. 4A-B, wherein the growth stent is shown in an expanded state for defining an internal channel with a first predetermined cross-section.
Figure 5A:
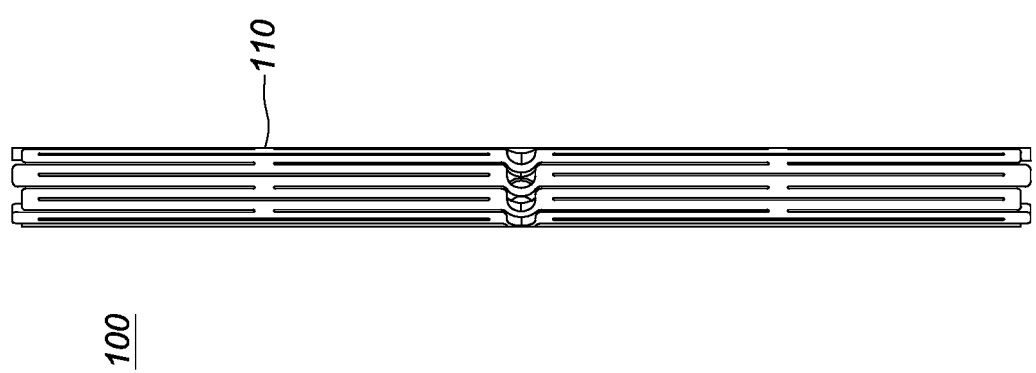
FIG. 5A is an exemplary detail diagram illustrating an embodiment of the growth stent of FIGS. 4A-B, wherein the growth stent is shown in an initial state for implantation.

Upon being positioned at a selected implantation site 310 (or other area of interest) (shown in FIGS. 8A-D) within the lumen 300, the stent body 110 can be expanded from the initial state to a first expanded state as shown in FIG. 5B. In the first expanded state, the stent body 110 can have a first predetermined expanded size, shape, diameter, cross-section and/or other dimension D. The stent body 110, when expanded in the first expanded state, can define the internal channel 120. The internal channel 120 can have a first predetermined diameter, cross-section and/or other dimension D for facilitating an unobstructed (or normal) flow of a bodily fluid, such as blood, bile or other luminal liquids, through the lumen 300 via the growth stent 100.

In selected embodiments, the expanded stent body 110 can comprise a body wall 112 that defines the internal channel 120 that preferably extends from a proximal end region 130 of the stent body 110 to a distal end region 140 of the stent body 110 as illustrated in FIG. 4A. The growth stent 100 thereby can enable the bodily fluid to flow, preferably unobstructed, from the proximal end region 130 to the distal end region 140 via the internal channel 120. Stated somewhat differently, the growth stent 100 can be provided in generally tubular shape and/or can support a valvular function in the manner discussed herein with reference to FIGS. 3A-B.

As shown in FIG. 4A, one or more selected junctions 170 of the stent body (or frame) 110 can be formed from frame members that include respective arcuate members, such as arcuate members 174, 176. The arcuate members 174, 176 each can define a central recess 172. The growth stent 100 can expand in the manner discussed herein such that the diameter, cross-section and/or other dimension D of the internal channel 120 can increase from a smaller dimension DA as shown in FIG. 4A to a larger dimension DB as shown in FIG. 4B in the manner discussed herein. The expansion of the growth stent 100 can comprise expansion between any two predetermined states. For example, the expansion of the growth stent 100 can comprise expansion from the initial state illustrated in FIG. 5A to the first expanded state illustrated in FIG. 5B, expansion from the first expanded state illustrated in FIG. 5B to the second expanded state illustrated in FIG. 5C and/or expansion from the second expanded state illustrated in FIG. 5C to the third expanded state illustrated in FIG. 5D, or any other expansion of the growth stent 100 without limitation.

As the growth stent 100 expands, the arcuate members 174, 176 can converge. The arcuate members 174, 176 thereby can cooperate such that the central recess 172 of the arcuate member 174 can cooperate with the central recess 172 of the arcuate member 176. The arcuate members 174, 176, in other words, can comprise cooperating arcuate members. The cooperating arcuate members 174, 176 thereby can define a central channel 178. The central channel 178 can be formed between the cooperating arcuate members 174, 176 and comprise an intersection of the central recess 172 of the arcuate member 174 and the central recess 172 of the arcuate member 176.

The arcuate members 174, 176 advantageously can provide axial flexibility for the growth stent frame 110, for example, if the arcuate members 174, 176 are thinner than the strut width 160 of the rest of the growth stent 100. In some embodiments, the arcuate members 174, 176 can utilize a "c-like" shape to allow deformation that is opposite of the usual column strength provided by the growth stent frame 110. The arcuate members 174, 176 can provide a lever point in the structure of the frame 110, potentially allowing for a bend in the frame 100 when tracking to a target location or potentially after deployment, depending on the configuration needed for either. The bend can occur by the "c-like" shape deforming to collapse upon itself and/or to open to be more of a straight line, depending on the direction of deformation.

In the manner discussed in more detail above with reference to FIGS. 1A-B and FIGS. 2A-D, the growth stent 100 of FIGS. 4A-B advantageously can be expanded to cover the wide range of anatomical diameters necessary to treat narrowed lesions across an entire lifetime of the patient. Stated somewhat differently, the predetermined number of expanded states supported by the growth stent 100 can configure the growth stent 100 to provide a wide range of anatomical diameters. The growth stent 100, for example, can be crimped on the delivery catheter 210 at small enough sizes for a neonatal patient, such as considerably less than an 8 French crimped growth stent 100, with an ability to be expanded later to teen and/or adult sizes of greater than 18 mm in diameter.

FIGS. 5A-D illustrate selected embodiments of a growth stent frame at various cycles throughout a patient's life, as the diameter of a vessel (or lumen) 300 (shown in FIGS. 8A-D) of the patient grows. In this specific example, the growth stent frame 110 can maintain strength at the various diameters. Turning to FIG. 5A, the growth stent 100 is shown in the initial state for implantation. The stent body 110, in the initial state, can have a predetermined initial size, shape, diameter, cross-section or other dimension of, for example, 2 mm for facilitating insertion of the growth stent 100 into the lumen 300.

Figure 5C:
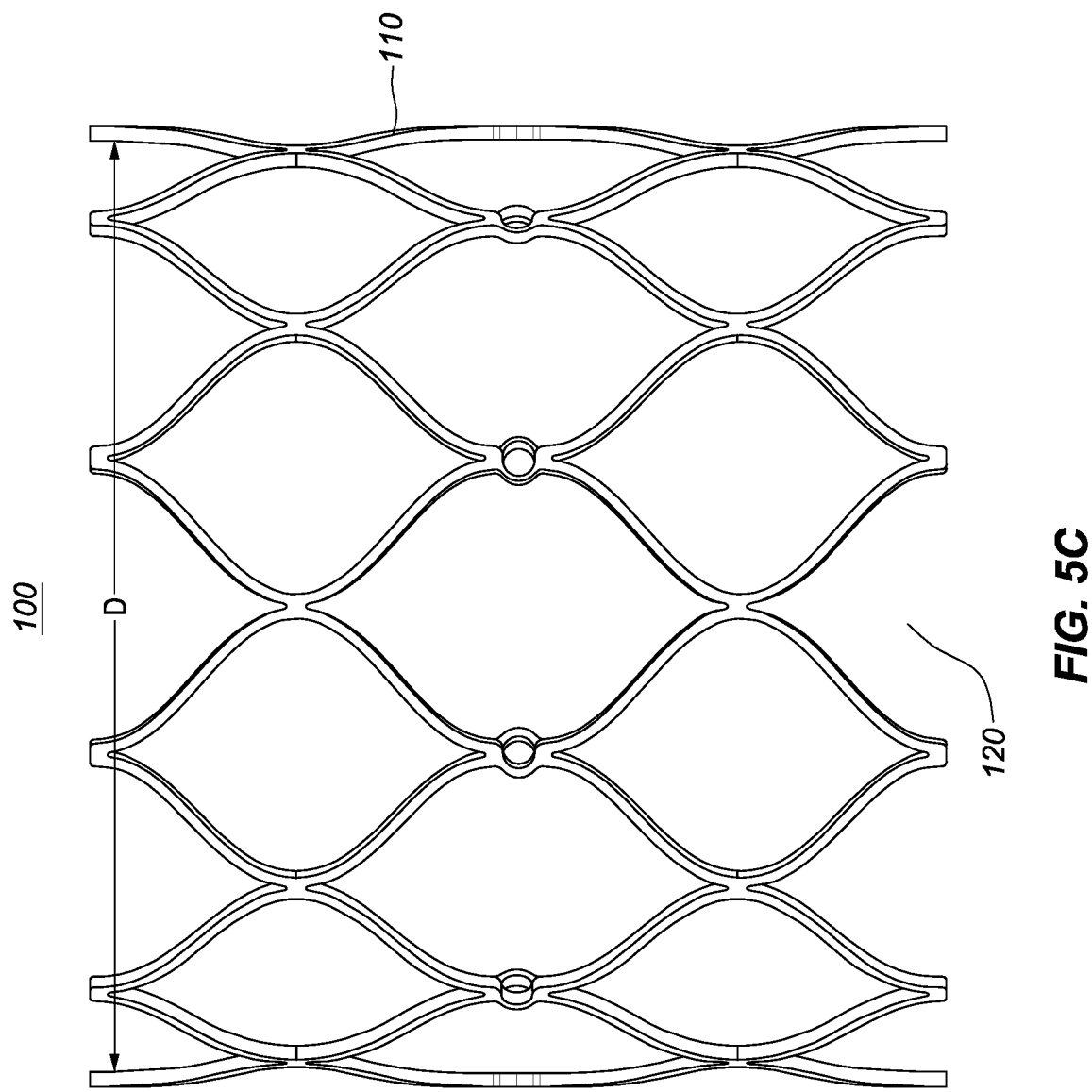
FIG. 5C is an exemplary detail diagram illustrating yet another alternative embodiment of the growth stent of FIGS. 4A-B, wherein the growth stent is shown in an expanded state for defining the internal channel with a second predetermined cross-section.
Figure 5D:
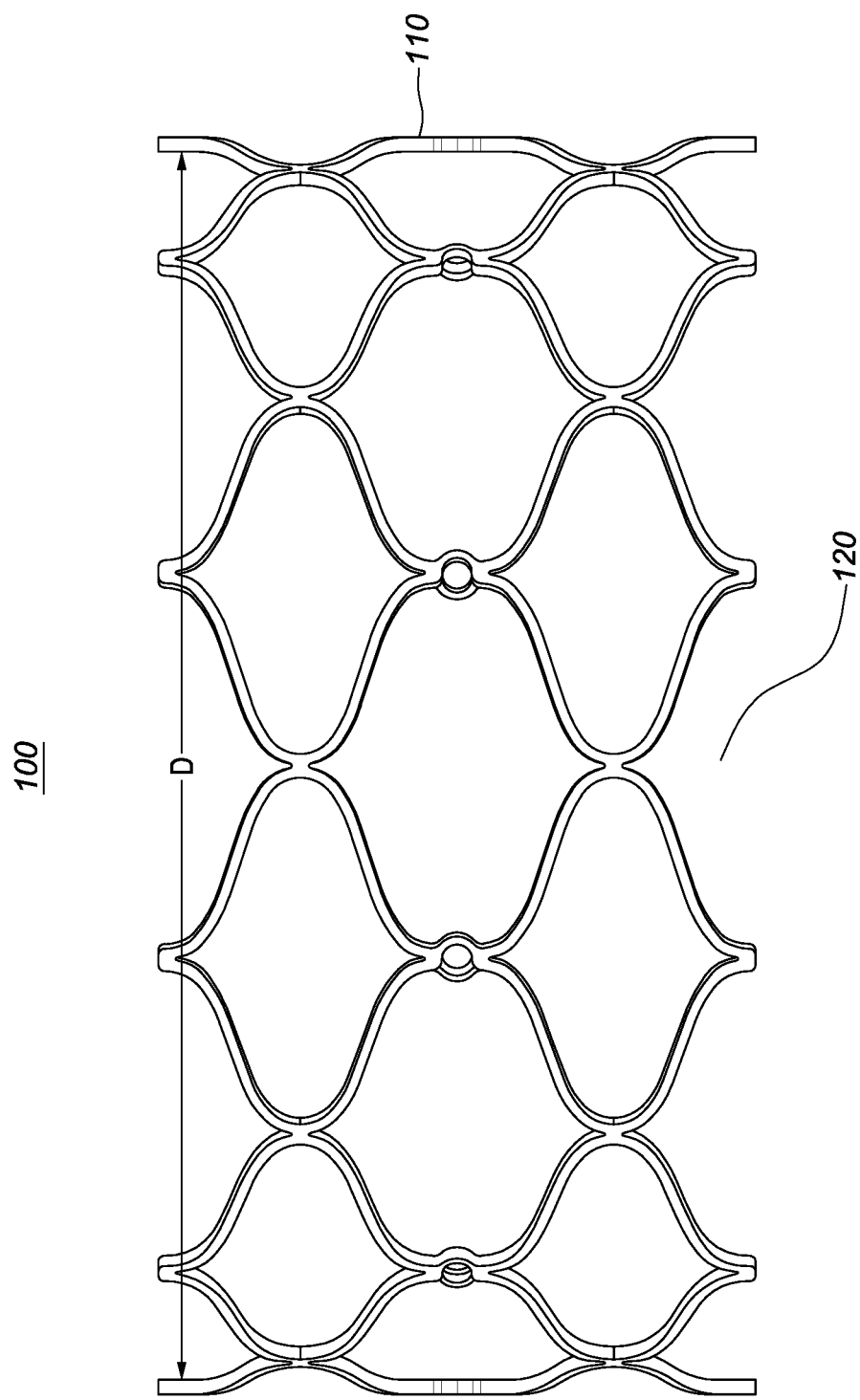
FIG. 5D is an exemplary detail diagram illustrating still another alternative embodiment of the growth stent of FIGS. 4A-B, wherein the growth stent is shown in an expanded state for defining the internal channel with a third predetermined cross-section.

When the growth stent 100 is in an expanded state, the stent body 110 can define the internal channel 120 with any suitable predetermined diameter, cross-section or other dimension D. The stent body 110, for example, can define the internal channel 120 with a first predetermined diameter, cross-section or other dimension D of 8 mm as shown in FIG. 5B, a second predetermined diameter, cross-section or other dimension D of 15 mm as shown in FIG. 5C and/or a third predetermined diameter, cross-section or other dimension D of 20 mm or more as shown in FIG. 5D, without limitation. The growth stent 100 thereby can be provided to hold open a narrow vessel 300 (shown in FIGS. 8A-D) and allow for normal flow of blood or other bodily fluids.

As an example, the growth stent 100 can be implanted in a vessel (or lumen) 300 (shown in FIGS. 8A-D) of an infantile patient through expansion to a diameter of less than 10 mm and have proper strength to be expanded over the course of a patient's lifetime to significantly greater than 18 mm. The exemplary growth stent 100 can be tracked through the vessel 300 of the infantile patient via a delivery catheter 210 of a catheter delivery system 200 (collectively shown in FIGS. 7A-B) that is considerably less than 8 French in diameter and, in some embodiments, less than 5 French in diameter and beyond.

Figure 6B:
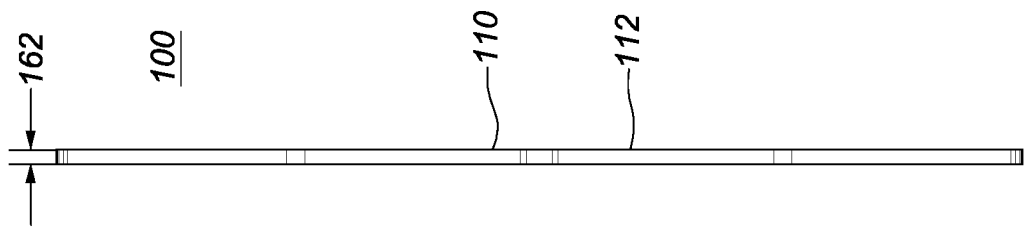
FIG. 6B is an exemplary detail diagram illustrating a side view of the growth stent of FIG. 6A.
Figure 6A:
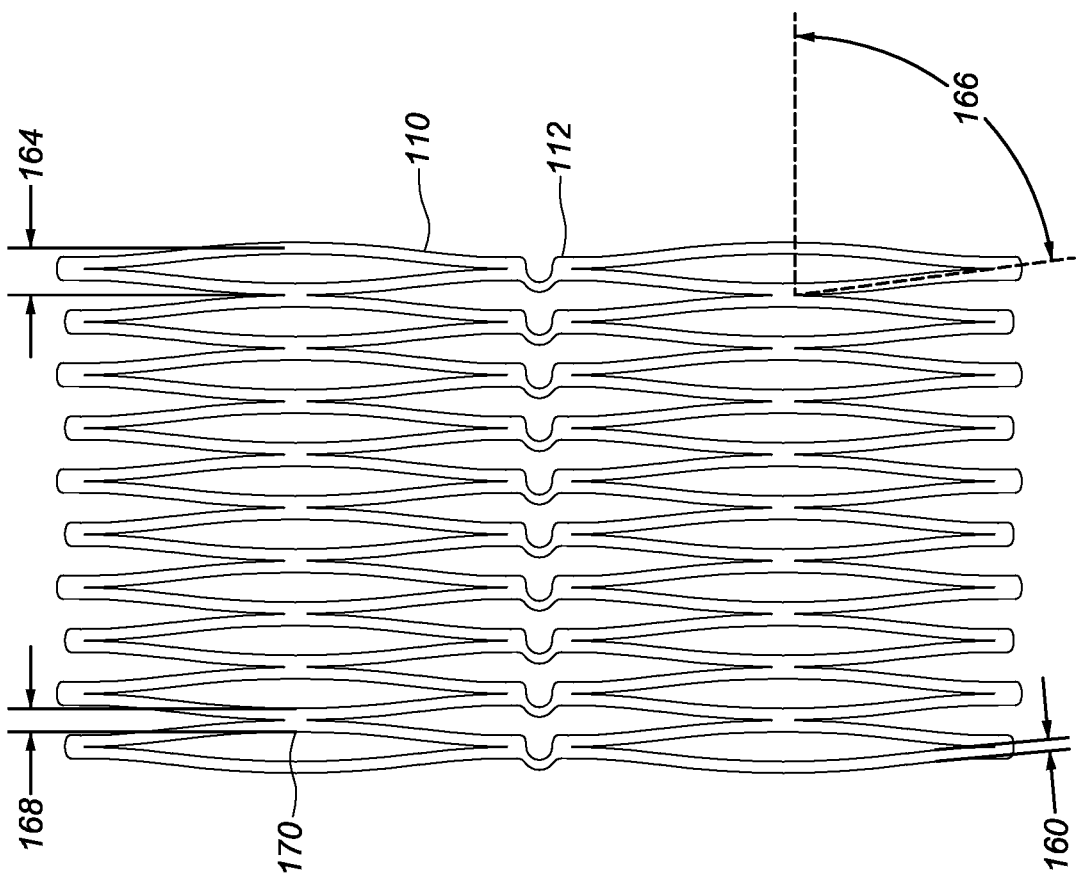
FIG. 6A is an exemplary detail diagram illustrating a two-dimensional flat view of the growth stent of FIGS. 4A-B.

Turning to FIGS. 6A-B, growth stent geometry, including frame strut width 160, frame thickness 162, number of cells 164, and/or cell angulation 166, can contribute to the ability to maintain strength over the wide range of deployments and expansions. Frame strut width 160 and frame thickness 162 can be employed to determine the radial force of the growth stent frame 110 with the number of cells 164 magnifying the impact of these characteristics. In one embodiment, the growth stent frame 110 can be optimized to lessen the impact of foreshortening of the growth stent 100. Foreshortening is the length shortening that can occur as the growth stent 100 is expanded from the crimped state into the selected expanded state. The cell angulation 166 and length of the growth stent cells 164 can be optimized to lessen the amount of growth stent foreshortening in order to more predictably deploy the growth stent 100 through expansion, such as balloon expansion.

The width of the strut junctions can contribute to an ability of the growth stent 100 to be crimped small enough to track through infantile blood vessels 300. Keeping the strut junction width 168 small to allow for the number of cells 164 in the growth stent 100 to be crimped smaller can help facilitate delivery. The junction width 168 preferably is large enough to expand over a large range for later expansion without significant frame stress and strain, leading to a small range in order to optimize the growth stent junction width 168 for this purpose. Growth stent frame material can enable these properties, allowing for strength across the wide range of operation despite the thin-walled nature of the growth stent 100 to allow the growth stent 100 to be crimped to small enough sizes to be delivered into neonatal patients.

The growth stent frame 110 may be optimized to allow for a thicker wall thickness 162 from the initial tubing utilized for the metal structure. Limiting junction width 168 to a minimum with relation to the strut width 160 can allow for an increase in wall thickness 162 of the frame 110, which can prevent the growth stent 100 from having a spring-like reaction when radial force is applied. Therefore, the crush resistance of the frame 110 can be increased, lessening the effect of recoil from the vessel 300, increasing the radial force of the growth stent 100 across all diameters necessary for expansion and providing a rigid structure to hold the vessel 300 open.

Because of the strength needed for this patient population and a desire for the frame to be crimped to exceedingly small diameters, specific formulas exist for calculating strut width 160, wall thickness 162, junction size, and number of cells 164 that create an optimized version that allows for re-expansion over the large range of use for the growth stent 100. One exemplary formula for optimizing the growth stent 100 is set forth in Equation 1. According to Equation 1, the smallest crimp diameter of the growth stent 100 can be represented as:

$$\frac{(SW+J)*N}{\pi} + (2*ST) \quad \text{(Equation 1)}$$

wherein SW represents a strut width 160, J represents a junction width 168, N represents a number of cells 164, and ST represents a strut thickness from the wall thickness 162 of the initial tubing. Equation 1 allows for certain parameters to be set based upon the recoil strength necessary to maintain proper strength across the desired range of use, by increasing the strut thickness 162 and maintaining the ability to be crimped to desired small diameters. By minimizing the junction as only slightly larger than the strut width 160 of the growth stent 100, the smallest crimp diameter may be calculated as a function of strut width 160 and junction width 168 multiplied by the number of cells 164 in accordance with Equation 1.

In some embodiments of the growth stent 100, a thickness 162 of the body (or frame) wall 112 can be minimized to prevent thrombus and/or stenosis of the vessel 300. Increasing the thickness 162 of the frame wall 112 can lessen the diameter of the vessel 300 after expansion as the frame wall 112 can provide blockage of the vessel 300. Additionally and/or alternatively, an increase in the thickness 162 of the frame wall 112 can provide more material for thrombus attachment. More material in the stent frame 110 can allow for more endothelization, allowing for cells 164 to attach to the foreign body.

In an optimized embodiment of the growth stent 100, the factors of strength and thickness 162 can be calculated to produce the best results for a growing patient. Utilizing vessel strength research, the growth stent frame may be optimized to allow for adequate strength across the varied range of operation utilizing one of more of the above factors. The growth stent 100 may have specific parameter ranges that are unique to this application, differentiating it from conventional stent frames. When attaching a resulting stent radial force and crush force as an output, for example, Equation 1 may be optimized for strength, allowing for an optimized stent frame 110 for growth over a specific range.

Equation 1 assumes that a measured length of the growth stent frame strut is constant and determined because changing the strut length can impact the output strength. In one optimized embodiment of the growth stent 100, the strut length can be determined to ensure that the stent frame 110 does not experience high levels of stress and strain that may lead to frame complications such as deformation and/or fracture. Increasing the length of the strut itself can increase the diameter of expansion but can decrease the resulting radial force. Therefore, an optimized embodiment of the growth stent 100 may contain the smallest strut length that allows for the stress and strain on the stent frame 110 to be acceptable across the intended diameter range of the growth stent 100.

Once the smallest strut length for the growth stent 100 is determined, Equation 1 may be utilized to optimize the frame 110. While two or more factors, or, in some cases, all factors may be changed in concert, certain parameter changes can show a pattern with regard to output radial strength of the frame 110, allowing for varied embodiments of the same stent structure to serve the purpose of a growth stent 100. In some embodiments of the growth stent 100, these parameters can be optimized for a small enough minimum crimp to not cause harm to vessels 300 of neonatal patients while providing adequate strength at large adult vessel sizes unlike commercially-available stents that are optimized for very specific adult-size diameter ranges.

The growth stent 100 preferably possesses adequate radial strength to keep the vessel 300 open at a specified diameter, such as by using the stent expansion system 260 (shown in FIG. 7A), such as a balloon, to expand the growth stent 100 to the specific diameter and the growth stent frame 110 containing enough radial strength to maintain the specific diameter without support from the balloon. However, radial strength and other properties of the growth stent 100 may affect the fatigue potential of the growth stent frame 110. Fatigue can result from continuous and repetitive motion creating stress and strain on the frame 110.

In some embodiments, one or more of the properties of the stent frame 110 can be optimized to ensure that unacceptable fatigue does not occur over the lifetime of the growth stent 100. This can be done in a variety of ways. Exemplary manners for avoiding unacceptable fatigue can include increasing the radial strength of the growth stent 100 to limit cyclical compression and expansion in the vessel 300 and/or increasing the length of the struts themselves to create more relaxed cell structures that are less susceptible to fatigue. The level of ductility in the metal or other material chosen for the stent frame 110 may also factor into the level of strain. Excess fatigue and strain on the growth stent frame 110 may lead to deformation and/or potential fracture of the metal or other material forming the growth stent 100.

In some embodiments of the growth stent 100, the frame 110 can be cut from a tube using a laser cutting machine (not shown). The laser cutting machine can finely cut through the wall thickness 162 of the tubing to create the cell structure. After cutting, the unwanted material can be stripped and/or removed from between the cell struts that have been cut. In many cases, the laser cutting machine can leave rough edges on the growth stent frame 110 and/or the metal frame, which preferably are sanded on the inner diameter to ensure no burrs remain.

Additionally and/or alternatively, some embodiments of the growth stent frame 110 can be electropolished to remove the outer layer of metal on the frame 110, smoothing the edges and finishing the frame 110 for implantation. Electropolishing in many instances uses electrical current through a liquid bath to evenly distribute the removal of material from the outer layers of the metal on the frame 110, often leaving the growth stent 100 with the appearance of shine from the polish. Some embodiments, such as frames utilizing NITINOL or other shape-changing materials, may be shape-set to desired shapes using heat and quenching.

The diameter of the tubing utilized as the base of the stent frame 110 may affect the strength of the frame 110. Larger diameter tubes are less trapezoidal if the wall thickness 162 of the tubing is maintained. While the stent frame 110 may be adjusted to be cut at any diameter of tube as long as the wall thickness 162 remains accurate, trapezoidal struts that occur from smaller tubes may lead to less radial strength over the desired range as the strut is made with less material. In an optimized version of the growth stent 100, the frame 110 can be cut from a specific tubing thickness 162 and/or diameter to ensure proper strength across the entire range of use.

In selected embodiments, the growth stent 100 may include a bare metal frame 110 and/or have a blood-impermeable covering on a segment of the frame 110. The blood-impermeable covering allows for vessel ingrowth and seals the vessel 300 from blood leaking through the growth stent 100. The covering may be of cloth material such as polyethylene terephthalate (PET) and/or a fluoropolymer, such as some polytetrafluoroethylenes. The covering seals and performs across the range of diameters of the growth stent frame 110 and is able to be expanded with the frame 110 over the lifetime of patient growth. In one embodiment, the blood-impermeable covering can be attached to each diamond-shaped cell of the growth stent 100, form-fitting to each cell. The cloth in this embodiment may be sewed or tacked onto the frame 110 using a suture or other suitable tacking method.

In one exemplary embodiment, the blood-impermeable covering can be attached at the distal and proximal ends 130, 140 (shown in FIGS. 1A-B) of the growth stent frame 110 and/or at one or more other predetermined locations along the growth stent frame 110 to allow for proper expansion. The covering may be attached in any suitable manner, such as through sewing and/or tacking in the manner set forth herein and/or through selective welds to ensure fixture to the frame 110. Additionally and/or alternatively, the growth stent frame 110 may be dipped in a polymer that forms a flexible webbing between the cells 164 of the frame 110 to provide a blood-impermeable covering. In this embodiment, the frame 110 can be dipped in a liquid polymer and slowly removed, allowing the polymer to dry and create the flexible covering after removal. The polymer may be cured in air and/or in an oven for desired material properties.

One or both end regions 130, 140 of the growth stent 100 may be flared outwardly relative to a longitudinal axis of the growth stent 100 in some embodiments. The flared end regions 130, 140 advantageously can help secure the growth stent 100 into place in the wall of the artery or other lumen. The flare may be implemented in any suitable manner. For example, the flare may be implemented by outwardly curving the tips of a selected end region 130, 140 using material properties and/or shape-setting. Another embodiment can use expansion from a balloon or other expandable member (not shown) with an outward curve shape. Additionally and/or alternatively, one or both end regions 130, 140 may be flared inwardly to prevent aneurysm using similar techniques.

Aneurysms may be similarly prevented through dulling one or both end regions 130, 140 of the growth stent 100. Dulled end regions 130, 140 may be created in the growth stent 100, in some embodiments, by attaching circular eyelets and/or ends of various sizes to lessen the sharpness of the growth stent frame 110. For example, the end regions 130, 140 may be circular, hooked, or have any other noninvasive shape. Another embodiment of the growth stent 100 can use features on the growth stent 100 to engage with the anatomy and keep the growth stent 100 in place. In this embodiment, the growth stent 100 can contain sharper edges cut into the growth stent frame 110 and/or may utilize a type of barb for fixturing, whether through the growth stent 110 or the addition of suture knots to provide fixation in the vessel 300.

In another embodiment of the stent frame 110, one or both of the end regions 130, 140 may have material removed with relation to the rest of the stent frame 110. The material can be removed, for example, from the strut width 160 of the frame 1, from the strut thickness 162 of the growth stent 100 or from both. Removing the material allows for the thinned end regions 130, 140 of the growth stent 100 to be more flexible than the thicker stent body 110, allowing for less blood vessel penetration and a potential to be less invasive in the patient's body. Flexibility may be utilized in this embodiment of the frame 110 to prevent aneurysms and vessel irritation. If the embodiment of the growth stent 110 is balloon dilatable, for example, the thinned end regions 130, 140 can cause less resistance to the balloon and may be utilized as tool to prevent movement of the growth stent 110 during deployment utilizing the balloon.

The end regions 130, 140 of the growth stent 100 can engage into the surrounding vessel 300 or other anatomy in the narrowed lesion using radial force. Flares at the end regions 130, 140 advantageously can be applied for securing the growth stent 100 to the surrounding anatomy. The flares serve as a stop, which can secure the growth stent 100 in place. When an axial force is applied to the growth stent 100, the flares can push into the surrounding anatomy to resist migration of the growth stent 100.

The flares and growth stent expansion may be done naturally through expanding properties of the growth stent 100, such as material choice, and/or manually through the use of a pressured balloon or other stent expansion system 260 to expand the frame 110 to a larger diameter than the vessel 300, stretching the walls of the vessel 300 and anchoring the growth stent 100 within the vessel 300 using radial strength. As the patient grows, the diameter of the growth stent 100 can increase through material properties and self-expansion and/or through a later balloon dilation to increase the diameter and ensure the growth stent 100 maintains fixation through over-expansion and resulting radial force of the frame 110.

The growth stent 100 may be made of one or more of a variety of conventional materials for balloon-expanding stents or, in alternative embodiments, for self-expandable growth stents. As non-limiting examples, the growth stent 100 may be made of any appropriate material, such as a metal or metal alloy, including stainless steel, cobalt chromium, NITINOL, or Elgiloy, or a polymer, for example. For self-expanding embodiments, the growth stent 100 can be made of a shape memory material such as, for example, NITINOL.

The growth stent 100 advantageously can be configured for delivery into narrowed vessels 300 with an ability to be expanded to a selected expanded state, such as an adult size, and maintain adequate strength for vessel openings over the entire range of necessary expansion. In selected embodiments, a transvascular technique can be used to introduce and implant the growth stent 100 in neonates and other young patients using a catheter delivery system 200 as shown in FIGS. 7A-B. Turning to FIG. 7A, the exemplary catheter delivery system 200 can comprise a flexible delivery catheter 210 and advantageously can introduce and implant the growth stent 100 in a manner that is less invasive than open heart surgery. The delivery catheter 210 can be trackable to a heart (or other implantation site 300 (shown in FIGS. 8A-D)) and surrounding vasculature through a vessel 300 in the groin or another connecting vessel 300.

An end portion 220 of the delivery catheter 210 is shown as including an inner shaft 240 and an outer shaft 250. One or more of the shafts 240, 250 can be made of a flexible plastic, such as Pebax or other Nylons and contain open lumens. The delivery catheter 210 preferably comprises a flexible catheter. The flexibility can allow for proper pushability through human vascular to allow the growth stent 100 to be delivered to a proper location. The plastics used for the delivery catheter 210 can be biocompatible as to not cause harm to the patient.

In selected embodiments, the growth stent 100 can be mounted in the initial (or crimped) state on the end portion 220 of the delivery catheter 210. In other words, the growth stent 100 in the initial state can receive the inner shaft 240 via the internal channel 120 (shown in FIGS. 1A-B). The growth stent 100 thereby can be disposed between the inner shaft 240 and the outer shaft 250 of the delivery catheter 210. The end portion 220 of the delivery catheter 210 likewise can include an optional stent expansion system 260, such as a balloon, for expanding the growth stent 100 from the initial state to a predetermined expanded state. In selected embodiments, the stent expansion system 260 can be at least partially disposed within the internal channel 120 to facilitate subsequent expansion of the growth stent 100.

Once the growth stent 100 is properly positioned on the end portion 220 of the delivery catheter 210, the catheter delivery system 200 can be provided in a closed configuration as illustrated in FIG. 7B. Stated somewhat differently, the catheter delivery system 200 can transition from an open configuration of FIG. 7A to the closed configuration of FIG. 7B. Turning to FIG. 7B, the outer shaft 250 of the delivery catheter 210 is shown as being moved distally toward an optional nosecone 230 of the delivery catheter 210. Stated somewhat differently, the growth stent 100 can be disposed between the inner shaft 240 and the outer shaft 250 when the delivery catheter 210 is in the closed configuration. The outer shaft 250 thereby can provide a protective shell for the growth stent 100 for introduction and advancement through a vessel (or lumen) 300 of a patient.

During implantation, the delivery catheter 210 of the catheter delivery system 200 can track through the vasculature with the growth stent 100 and stent expansion system 260 covered by the outer shaft 250. The delivery catheter 210 thereby can be advanced through the vessel (or lumen) 300 of a patient until the end portion 220 reaches an implantation site 310, such as a narrowed lesion or other diseased area, as illustrated in FIG. 8A. Upon becoming disposed adjacent to the implantation site 310, the catheter delivery system 200 can be provided in an open configuration as illustrated in FIG. 8B. Stated somewhat differently, the catheter delivery system 200 can transition from the closed configuration of FIG. 7B to the open configuration of FIG. 8B.

Figure 8C:
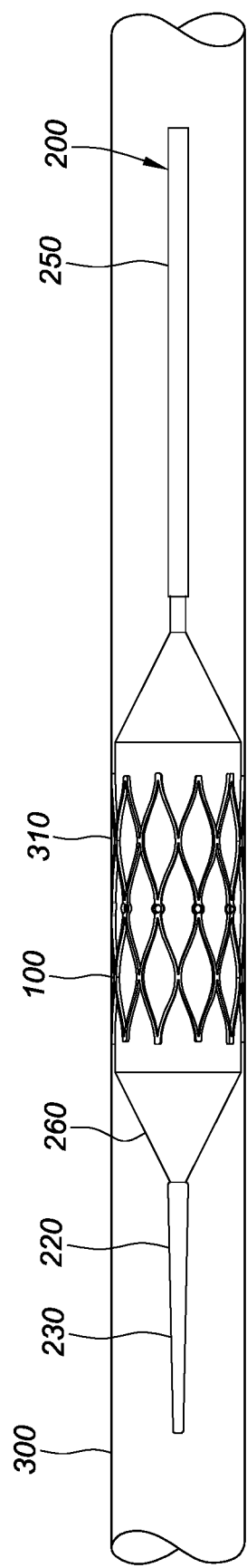
FIG. 8C is exemplary detail diagram illustrating an embodiment of the catheter delivery system of FIG. 8B, wherein the catheter delivery system expands the growth stent from an initial state to an expanded state.

In the open configuration, the outer shaft 250 of the delivery catheter 210 can be disposed proximally or away from the nosecone 230. The delivery catheter 210 thereby can expose the growth stent 100 to the implantation site 310. With the growth stent 100 adjacent to the implantation site 310, the stent expansion system 260 can be activated to expand the growth stent 100 from the initial (or unexpanded or crimped) state as shown in FIG. 8B to the first expanded state of FIG. 8C. In selected embodiments, the stent expansion system 260 can include a balloon that can be inflated to expand the growth stent 100.

Additionally and/or alternatively, the growth stent 100 optionally can be expanded by expanding a distal portion of the growth stent 100 while a proximal portion of the growth stent 100 is anchored to the delivery catheter 210 without use of the stent expansion system 260. Once the distal portion of the growth stent 100 is expanded, the proximal portion of the growth stent 100 can be disengaged from the delivery catheter 210 and expanded into the lumen 300. The proximal portion of the growth stent 100, for example, may be expanded all at once or in stages.

Figure 8D:
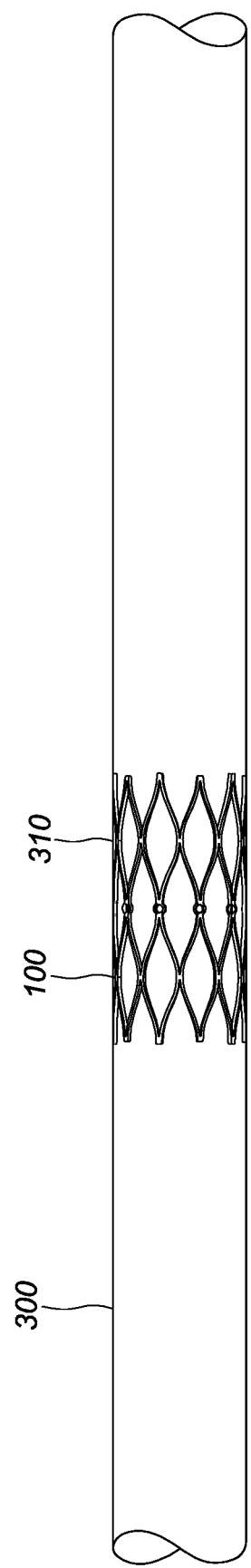
FIG. 8D is exemplary detail diagram illustrating an embodiment of the catheter delivery system of FIG. 8C, wherein the catheter delivery system is withdrawn from the implantation site, leaving the expanded growth stent.

In the first expanded state, the growth stent 100 can have a first predetermined expanded size, shape, diameter, cross-section and/or other dimension in the manner set forth in more detail above with reference to FIG. 1A. The stent expansion system 260 can be deactivated, retracting to an initial size. If the stent expansion system 260 includes the balloon, the balloon can be deflated. The delivery catheter 210 then can be withdrawn from the lumen 300 once the growth stent 100 in the first expanded state is successfully deployed at the implantation site 310 as shown in FIG. 8D.

The growth stent 100 thereby can be implanted with its functional size at the implantation site 310. As needed, the growth stent 100 can be further expanded to a larger size, such as a teen size and/or adult size, a later date. In a manner similar to the implantation, for example, another delivery catheter 210 can track through the vasculature of the patient and be advanced through the vessel 300 until the end portion 220 reaches the growth stent 100 at the implantation site 310. A stent expansion system 260 of the delivery catheter 210 can be disposed within the internal channel 120 (shown in FIG. 1A) of the growth stent 100 and activated to expand the growth stent 100 from the first expanded state of FIG. 8C to a second expanded state of FIG. 1B.

In the second expanded state, the growth stent 100 can have a second predetermined expanded size, shape, diameter, cross-section and/or other dimension, which is greater than the first predetermined expanded size, shape, diameter, cross-section and/or other dimension of the growth stent 100 in the first expanded state, in the manner set forth in more detail above with reference to FIG. 1B. The stent expansion system 260 can be retracted, and the delivery catheter 210 can be withdrawn from the lumen 300 once the growth stent 100 in the second expanded state is successfully deployed at the implantation site 310 in the manner set forth above with reference to FIG. 8D.

The growth stent 100 advantageously can be implanted in a neonate patient and expanded as needed throughout the lifetime of the patient. Once delivered and implanted at a certain diameter, the growth stent 100 can be expanded to a larger size at a later time. This applies in the case that the vessels initially receiving one embodiment of the growth stent 100 are continuing to grow, such as throughout the growth of the patient from infancy to adolescence and adulthood. Because the growth stent 100 can have proper strength over all applicable ranges of growth, a separate balloon or other stent expansion system 260 at a later point in the growth cycle of the patient can be tracked to the growth stent 100 at the implantation site 310. This further expansion of the growth stent 100 can occur as necessary for the growth of an individual patient.

Figure 9:
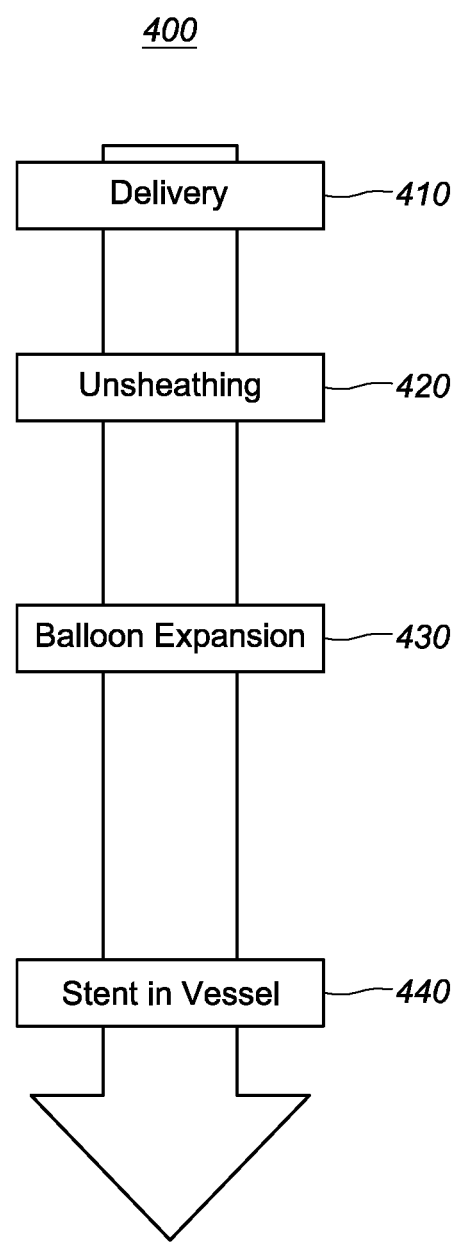
FIG. 9 is an exemplary flow chart illustrating an embodiment of a method for implanting of the growth stent of FIGS. 1A-B via a balloon catheter delivery system.

In selected embodiments, the delivery catheter 210 can comprise a balloon catheter with a balloon 260 for expanding the growth catheter 100. The balloon catheter can introduce and deploy the growth stent 100 in a manner analogous to the manner by the delivery catheter 210 is described as introducing and deploying the growth stent 100 with reference to FIGS. 8A-D. Turning to FIG. 9, for example, an exemplary method 400 for implanting the growth stent 100 (shown in FIGS. 8A-D) via a balloon catheter system is shown. The method 400 includes delivering the growth stent 100 to the implantation site 310 of the vessel (or lumen) 300 of a patient (collectively shown in FIGS. 8A-D), at 410. The balloon catheter can be advanced through the vessel (or lumen) 300 of a patient until reaching the implantation site 310.

Upon becoming disposed adjacent to the implantation site 310, the balloon catheter can be provided in an open configuration, or unsheathed, at 420, exposing the growth stent 100 to the implantation site 310. Stated somewhat differently, the catheter delivery system 200 can transition from the closed configuration of FIG. 7B to the open configuration of FIG. 8B. The balloon 260 can be filled with fluid and thereby expand in size, at 430. Being disposed in the internal channel 120 (shown in FIGS. 1A-B) of the growth stent 100, the expanding balloon 260 can expand the growth stent 100 from the initial (or unexpanded or crimped) state as shown in FIG. 8B to the first expanded state of FIG. 8C.

The growth stent 100 in the first expanded state thus can engage, and/or become embedded into, a wall of the vessel 300 at the implantation site 310, at 440. The balloon 260 then can be re-compressed and removed from the patient's body, leaving the growth stent 100 engaged with the vessel 300. In other words, the growth stent 100 can be introduced in the initial state and, once expanded by the balloon 260, can hold the vessel 300 open without the support of the balloon 260 after the balloon dilation. The growth stent 100 in the first expanded state thereby can be successfully deployed at the implantation site 310.

Additionally and/or alternatively, the balloon catheter can include the optional nosecone 230 (shown in FIGS. 7A-B). The nosecone 230 can aid with transitions and trackability through the vessel 300 and serve as a containing end region for the balloon 260 itself. The nosecone 230 can be designed using similar plastics as the shafts 240, 250, often with a triangular shape to aid with transitions and tracking through vessels 300. The balloon 260 advantageously can be designed with a thin plastic wall that is able to be compressed to fit inside of the delivery catheter 210 and ensure the profile is small enough to be inserted in the desired patient's vasculature. The balloon 260 can be attached to the inner plastic shaft 240 and sealed on the distal end. The inner lumen of the plastic shaft 240 can channel inserted fluid, such as saline, from the proximal end of the shaft to the balloon 260. As the balloon 260 fills with liquid, the balloon 260 can expand to the designed diameter.

When the growth stent 100 is crimped onto the balloon 260, the balloon 260 may be compressed to small diameters and without built in shoulders to hold the growth stent 100 in place. When retracting an outer shaft 250 to expose the growth stent 100 on the balloon 260, the balloon 260 may not have enough resistance to maintain the positioning of the growth stent 100 on the balloon 260. In certain embodiments, retracting the outer shaft 250 to expose the growth stent 100 may cause the outer shaft 250 to latch onto the growth stent 100 and pull the growth stent 100 off of the balloon 260.

In some embodiments of the balloon catheter, this issue may be mitigated through the use of a separate catheter (not shown) disposed between the balloon shaft and the outer shaft 250. This middle catheter may be utilized as a back stop for the growth stent 100 during outer shaft retraction. In this embodiment, the outer shaft 250 can be retracted over the growth stent 100 and the middle catheter as the middle catheter is fixed in relation to the balloon catheter, keeping the growth stent 100 in place during exposition. After the growth stent 100 and middle catheter are exposed, the middle catheter may then be retracted from over the balloon 260 to allow for expansion. This ensures that the growth stent 100 remains crimped in the proper position for balloon expansion at the target location 310 in the body of the patient.

In another alternative embodiment of the balloon catheter, instead of a back stop for the growth stent 100, the middle catheter can overlaps with the growth stent 100, creating a sock-like attachment to hold the growth stent 100 in place. This thin sock-like catheter can maintain stent positioning during outer shaft 250 retraction and allow for proper balloon 260 inflation. In some embodiments this sock-like catheter can be retracted before balloon 260 expansion if it overlaps with the growth stent 100. In other alternative embodiments, the sock-like catheter may only overlap the balloon 260 and may be expanded with the balloon 260 and removed with the balloon catheter.

In embodiments of the catheter delivery system 200 that contain the growth stent 100 crimped onto the balloon 260, the growth stent 100 can expand with the balloon 260 because of the radial pressure from the filled liquid. As liquid is removed from the balloon 260, back pressure can bring the balloon 260 back to its original compressed state, leaving the expanded growth stent 100 separated from the balloon 260 and the balloon catheter. In one embodiment, the balloon catheter may have a handle on the proximal ends of the shafts 240, 250 to connect the shafts 240, 250, seal the lumens to prevent blood leak and/or provide an ergonomic grip for an operator. The handle can be made of a hard plastic, soft silicone, and/or other solid materials. The embodiment may also contain an inner-most lumen to track over a guidewire (not shown) in the vasculature. The guidewire can provide a tracking rail to ensure the balloon catheter reaches the target location 310 and can be inserted into a lumen on the delivery system.

In selected embodiments, the delivery catheter 210 is advanced to the target location 310 by way of a femoral vein or artery, depending on the endpoint. Other vessels 300 in the patient may be utilized to properly track the delivery catheter 310 to the target location 310. The transitions in the material of the delivery catheter 210 allow proper trackability to the target location 310 despite difficult anatomy.

Additionally and/or alternatively, the catheter delivery system 200 can optionally flush air out of the delivery catheter 210 before the delivery catheter 210 is introduced into the body of the patient to prevent the addition of air molecules into the bloodstream that may cause embolization and other issues in the vessel 300. Flushing air out of a delivery catheter 210 may include, for example, flushing air out of the delivery catheter 210 with pressurized fluid. The catheter delivery system 200 can include the delivery catheter 210 and one or more inner lumens (not shown) at least partially disposed within the delivery catheter 210. The inner lumens can define at least one opening for a guidewire (not shown) and at least one opening connected to a balloon. Fluid can introduced into the inner lumens in the opening for a guidewire with at least some of the introduced fluid exiting the inner lumens through a distal opening to remove the air from the delivery catheter 210.

The sizing of the delivered growth stent 100 can allow the growth stent 100 to be safer for neonates and other younger patients. The growth stent 100, in one embodiment, can be delivered at an outer diameter of less than 2.5 millimeters when in a crimped state, while allowing for later expansion to over 20 millimeters in outer diameter in a fully expanded state.

The forgoing primarily describes embodiments of the growth stent 100 that are balloon-expandable for purposes of illustration only, not for purposes of limitation. It will be appreciated, however, that the catheter delivery system 200 shown and described herein can be readily modified for delivery of self-expandable growth stents, prosthetic heart valves and/or other medical devices. In other words, delivering self-expandable growth stents to an implantation location can be performed percutaneously using modified versions of the delivery devices of the present disclosure. In general terms, an exemplary modified version of the delivery devices can include a transcatheter assembly (not shown) with a delivery sheath and/or additional sheaths as described above. The devices generally further include a delivery catheter, a balloon catheter, and/or a guide wire.

Current market growth stents are unable to cover the total range necessary for the lifetime of the lesion in the patient, specifically a pediatric patient with congenital or anatomical disease. In this case, the growth stent may start small enough to be delivered safely into a neonate but is unable to grow to the adult size. Conversely, a growth stent that expands to large enough for the adult lesion cannot be crimped small enough to be safely implanted in a neonate on a catheter, as neonatal vessels are considerable smaller than an adult vessel.

Varied congenital disease states can be defined as narrowed lesions, such as Tetralogy of Fallot, Aortic Coarctation, various atresia, and various stenosis.

A further understanding of the nature and advantages of the growth stent 100 will become apparent by reference to the remaining portions of the specification and drawings. Variations and the optional features noted above may be added to embodiments of the growth stent 100, either alone or in various combinations, as appropriate. Specific numerical values for sizes, shapes, diameters, cross-sections or other dimensions are set forth herein for purposes of illustration only and not for purposes of limitation.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A catheter insertable and re-expandable growth stent for implantation in a neonate patient, comprising:
    an elongated stent frame with a plurality of frame struts each extending continuously from a proximal end region of said stent frame to a distal end region of said stent frame and having a uniform strut width, adjacent frame struts defining intermediate frame cells and intersecting to form respective strut junctions by which said elongated stent frame expands via a delivery catheter from an initial state for facilitating insertion via the delivery catheter into a selected vessel of the neonate patient to a first stable expanded state configured to support the selected vessel at implantation, said stent frame in the first expanded state defining an internal channel with a first cross-section,
    wherein said stent frame is configured to be re-expanded via subsequent introduction of a dilation catheter from the first expanded state to a second stable expanded state as the patient grows, said stent frame in the second expanded state continuing to support the selected vessel and defining the internal channel with a second cross-section being larger than the first cross-section.

2. The growth stent of claim 1, wherein said stent frame in the initial state has a small implantation size for facilitating insertion into the neonate patient.

3. The growth stent of claim 2, wherein the implantation size is less than 8 French.

4. The growth stent of claim 2, wherein the first cross-section is less than 10 millimeters.

5. The growth stent of claim 1, wherein said stent frame is configured to be re-expanded to the second expanded state after the neonate patient grows to become a child.

6. The growth stent of claim 5, wherein the second cross-section is between 10 millimeters and 15 millimeters, inclusive.

7. The growth stent of claim 1, wherein said stent frame is configured to further expand from the second expanded state to a third stable expanded state as the patient further grows, said stent frame in the third expanded state continuing to support the selected vessel and defining the internal channel with a third cross-section being larger than the second cross-section.

8. The growth stent of claim 7, wherein said stent frame is configured to be expanded to the third expanded state after the patient grows to become an adult.

9. The growth stent of claim 7, wherein the third cross-section is between 18 millimeters and 24 millimeters, inclusive.

10. The growth stent of claim 1, wherein said stent frame is provided with a tubular shape.

11. The growth stent of claim 1, wherein a strut junction between selected frame struts having a junction width that is sufficiently small for facilitating insertion of said stent frame in the initial state and that is sufficiently large for supporting expansion of said stent frame to the first and second expanded states while maintaining strength for supporting the selected vessel.

12. The growth stent of claim 1, wherein the internal channel extends between opposite end regions of said stent frame, at least one of the end regions being flared radially outwardly for facilitating an engagement between said stent frame and the selected vessel.

13. The growth stent of claim 1, wherein the internal channel extends between opposite end regions of said stent frame, at least one of the end regions being flared radially inwardly or being dulled for reducing risk of an aneurism in the selected vessel.

14. The growth stent of claim 1, wherein said stent frame includes a fluid-impermeable covering for preventing leaks due to ingrowth of the selected vessel as the patient grows.

15. The growth stent of claim 1, wherein said elongated stent frame is made of stainless steel, cobalt chromium, a polymer or a combination thereof.

16. The growth stent of claim 1, wherein the intermediate frame cells are enclosed by the adjacent frame struts.

17. The growth stent of claim 1, wherein two selected pairs of the adjacent frame struts intersect to define one of the intermediate frame cells and to form a plurality of the strut junctions.

18. The growth stent of claim 1, wherein two pairs of the adjacent frame struts intersect to define one of the intermediate frame cells and to form a plurality of the strut junctions.

19. A catheter insertable and re-expandable growth stent for implantation in a neonate patient, comprising:
an elongated stent frame with a plurality of frame struts each extending continuously from a proximal end region of said stent frame to a distal end region of said stent frame and having a uniform strut width, adjacent frame struts defining intermediate frame cells and intersecting to form respective strut junctions by which said elongated stent frame expands via a delivery catheter from an initial state for facilitating insertion via the delivery catheter into a selected vessel of the neonate patient to a first stable expanded state configured to support the selected vessel at implantation, said stent frame in the first expanded state defining an internal channel with a first cross-section,
wherein said stent frame is configured to be re-expanded via subsequent introduction of a dilation catheter from the first expanded state to a second stable expanded state as the patient grows into a teenage patient, said stent frame in the second expanded state being configured to continue to support the selected-vessel and defining the internal channel with a second cross-section being larger than the first cross-section, and
wherein said stent frame is further configured to be re-expanded via subsequent introduction of a second dilation catheter from the second expanded state to a third stable expanded state as the teenage patient further grows into an adult patient, said stent frame in the third expanded state being configured to continue to support the selected vessel and defining the internal channel with a third cross-section being larger than the second cross-section.

20. The growth stent of claim 19, wherein said stent frame in the initial state has an implantation size that is less than 8 French.

21. The growth stent of claim 19, wherein said elongated stent frame is made of stainless steel, cobalt chromium, a polymer or a combination thereof.

22. The growth stent of claim 19, wherein the intermediate frame cells are enclosed by the adjacent frame struts.

23. The growth stent of claim 19, wherein two selected pairs of the adjacent frame struts intersect to define one of the intermediate frame cells and to form a plurality of the strut junctions.

24. The growth stent of claim 19, wherein two pairs of the adjacent frame struts intersect to define one of the intermediate frame cells and to form a plurality of the strut junctions.

25. The growth stent of claim 19, wherein the first cross-section is less than 8 millimeters.

26. The growth stent of claim 19, wherein the second cross-section is 15 millimeters.

27. The growth stent of claim 19, wherein the third cross-section is between 18 millimeters and 24 millimeters, inclusive.

* * * * *

UNITED STATES PATENT AND TRADEMARK OFFICE
CERTIFICATE OF CORRECTION

PATENT NO. : 10,702,407 B1
APPLICATION NO. : 16/441201
DATED : July 7, 2020
INVENTOR(S) : Armer et al.

It is certified that error appears in the above-identified patent and that said Letters Patent is hereby corrected as shown below:

In the Specification

Column 8, Line 47, change "one of more" to --one or more--.
Column 10, Lines 24-25, change "the distal and proximal ends 130, 140" to --the proximal and distal end regions 130, 140--.
Column 10, Line 65, change "growth stent 110" to --growth stent frame 110--.
Column 11, Line 5, change "frame 1" to --growth stent frame 110--.
Column 11, Line 12, change "growth stent 110" to --growth stent 100--.
Column 11, Line 15, change "growth stent 110" to --growth stent 100--.
Column 13, Line 58, change "growth catheter 100" to --growth stent 100--.
Column 15, Line 38, change "catheter 310" to --catheter 210--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*